US011298206B2

(12) United States Patent
Chen et al.

(10) Patent No.: US 11,298,206 B2
(45) Date of Patent: Apr. 12, 2022

(54) POSITIONING SYSTEM FOR AN IMAGING DEVICE

(71) Applicant: The General Hospital Corporation, Boston, MA (US)

(72) Inventors: Yi Chen, Tubingen (DE); Xin Yu, Tubingen (DE); Shanyi Yu, Tubingen (DE)

(73) Assignee: The General Hospital Corporation, Boston, MA (US)

( * ) Notice: Subject to any disclaimer, the term of this patent is extended or adjusted under 35 U.S.C. 154(b) by 317 days.

(21) Appl. No.: 15/728,794

(22) Filed: Oct. 10, 2017

(65) Prior Publication Data

US 2018/0116759 A1    May 3, 2018

(30) Foreign Application Priority Data

Oct. 27, 2016 (EP) .................................... 16195972

(51) Int. Cl.
*A61B 90/50* (2016.01)
*A61B 34/20* (2016.01)
(Continued)

(52) U.S. Cl.
CPC .............. *A61B 90/50* (2016.02); *A61B 5/055* (2013.01); *A61B 5/061* (2013.01); *A61B 34/20* (2016.02);
(Continued)

(58) Field of Classification Search
CPC .... A61B 2034/2046; A61B 2034/2055; A61B 2090/0811; A61B 34/20; A61B 34/30;
(Continued)

(56) References Cited

U.S. PATENT DOCUMENTS

2009/0247944 A1* 10/2009 Kirschenman ......... A61B 34/37
604/95.04
2011/0118756 A1* 5/2011 Brock .................... A61B 34/71
606/130
(Continued)

FOREIGN PATENT DOCUMENTS

JP    2007289675    * 11/2007    ............. A61B 19/00

OTHER PUBLICATIONS

Labcompare (https://www.labcompare.com/6083-MRI-System-Magnetic-Resonance-Imaging-System/3660662-Discovery-MR901-System/) Discovery MR901 System from Agilent Technologies, Features, p. 3; Nov. 1, 2010. (Year: 2010).*
Extended European Search Report corresponding to Foreign Priority European Application No. 16195972.1, dated May 22, 2017.
Larson et al., "A robotic device for minimally invasive breast interventions with real-time MRI guidance," Mar. 10, 2003, Bio-informatics and Bioengineering, Proceedings, Third IEEE Symposium on Mar. 10-12, 2003, Piscataway, NJ, USA; pp. 190-197.
(Continued)

*Primary Examiner* — Pascal M Bui Pho
*Assistant Examiner* — Alexei Bykhovski
(74) *Attorney, Agent, or Firm* — Leydig, Voit & Mayer, Ltd.

(57) ABSTRACT

A positioning system for an imaging device, in particular a MR imaging device to position an insertion element on or in the body of a subject, in particular an animal, wherein the imaging device comprises a bore, in which the subject is received, wherein the positioning system comprises a robot which can be at least partially arranged in the bore of the imaging device and comprises a holding element to hold the insertion element; wherein the robot further comprises at least one actuator acting on the holding element, such that an end portion of the insertion element is movable, wherein said at least one actuator is arranged with a distance D from the bore to minimize magnetic and/or electromagnetic interferences between the imaging device and the at least one actuator and said first actuator is coupled to the holding element in a form-fit- and/or a force-fit-manner.

20 Claims, 12 Drawing Sheets

(51) Int. Cl.
*A61B 90/00* (2016.01)
*B25J 9/04* (2006.01)
*A61B 34/30* (2016.01)
*A61B 5/055* (2006.01)
*A61B 5/06* (2006.01)
*G01R 33/28* (2006.01)
*G01R 33/48* (2006.01)
*A61B 5/00* (2006.01)

(52) U.S. Cl.
CPC .............. *A61B 34/30* (2016.02); *A61B 90/39* (2016.02); *B25J 9/04* (2013.01); *G01R 33/286* (2013.01); *A61B 5/0071* (2013.01); *A61B 5/0084* (2013.01); *A61B 2034/2046* (2016.02); *A61B 2034/2055* (2016.02); *A61B 2090/0811* (2016.02); *G01R 33/4806* (2013.01); *G01R 33/4808* (2013.01)

(58) Field of Classification Search
CPC ..... A61B 5/0071; A61B 5/0084; A61B 5/055; A61B 5/061; A61B 90/39; A61B 90/50; B25J 9/04; G01R 33/286; G01R 33/4806; G01R 33/4808
See application file for complete search history.

(56) References Cited

U.S. PATENT DOCUMENTS

| | | | | |
|---|---|---|---|---|
| 2011/0296966 | A1* | 12/2011 | Oki ........................ | B26D 1/46 83/421 |
| 2012/0165904 | A1* | 6/2012 | Lee ...................... | A61B 5/0042 607/90 |
| 2014/0371584 | A1* | 12/2014 | Cleary .................. | A61B 34/30 600/431 |
| 2018/0199850 | A1* | 7/2018 | Lee ........................ | A61N 1/086 |
| 2019/0099227 | A1* | 4/2019 | Rockrohr ............... | A61B 34/30 |

OTHER PUBLICATIONS

Christoforou et al., "Design and Testing of a Robotic System for MR Image-Guided Interventions," Sep. 28, 2006, Journal of Intelligent and Robotic Systems, vol. 47, pp. 175-196.

Mylonas et al., "MR compatible positioning device for guiding a focused ultrasound system for the treatment of brain diseases," Jun. 7, 2013, International Journal of Medical Robotics and Computer Assisted Surgery, vol. 10, No. 1, pp. 1-10.

* cited by examiner

POSITIONING SYSTEM FOR AN IMAGING DEVICE

CROSS-REFERENCE TO RELATED APPLICATIONS

This application claims the benefit of and priority to EP App. No. 16195972.1, filed Oct. 27, 2016, which is hereby incorporated by reference in its entirety to the extent not inconsistent herewith.

BACKGROUND

The invention relates to a positioning system for an imaging device, in particular a MR imaging device, to position an insertion element on or in the body of a subject, in particular an animal, wherein the imaging device comprises a bore, in which the subject is received, wherein the positioning system comprises a robot, which can be at least partially arranged in the bore of the imaging device and comprises a holding element to hold the insertion element.

Brain intervention techniques are primarily used to treat patients with severe brain diseases, e.g. epilepsy, Parkinson disease, clinical depression or brain tumors. Deep brain stimulation is a key model to show how brain intervention could be directly used as a therapeutic strategy to treat patients. How to precisely target the specific functional nuclei of the diseased human brain and reduce the collateral tissue damage is a key challenge of the brain interventional clinical practice. The human brain MRI is usually used to help localize the target, as well as monitor the surgical procedure.

Magnetic resonance imaging (MRI), or Nuclear magnetic resonance imaging (NMRI), is an imaging technique to visualize the structure and function of tissue. This imaging technique provides detailed images of the tissue in any plane and a greater contrast between the different soft tissues compared to computer tomography (CT). Thus, it is especially favorable in neurological (brain), musculoskeletal, cardiovascular, and oncological (cancer) imaging. MRI utilizes a powerful magnetic field to align the nuclear magnetization of hydrogen atoms in the tissue. This alignment is then systematically altered by radiofrequency fields (RF). The hydrogen nuclei produce a rotating magnetic field detectable by the scanner. Such a signal can be manipulated by additional magnetic fields to build up information to construct an image of the body. By now Functional Magnetic Resonance Imaging (fMRI) has come to dominate the field of brain mapping. fMRI directly detects the hemodynamic signal from vessels, such as the blood-oxygen-level dependent (BOLD) contrast. Hereby the neural activity in the brain is mapped by imaging the change in blood flow/volume (hemodynamic response) related to energy consumption by brain cells.

The use of the high magnetic fields in the MRI-system makes the design of MRI-compatible robots difficult, since most of the components commonly used in robotics are unsuitable in close proximity of the MRI-device. In such a range ferromagnetic materials are exposed to very high magnetic interaction. Thus, strong forces may act on individual parts. Further, heating may occur in conductive materials by electromagnetic induction. Additionally, the use of electricity may cause interference-effects in the RF coils of the imager which can create image artifacts.

There are a few existing MRI-compatible or based devices that help better perform the procedure. However, the MRI-guided strategy is usually used as an assisting or verification procedure. The main surgical procedure remains to be done by neurosurgeons. There is long way to evolve from manual procedure to full automation. Besides technical limits, the safety and human brain complexity are the main limiting factors.

In contrast to the human brain/body intervention, there is less safety concern for animal brain surgeries. Moreover, animal brain studies are aimed to better understand the complexity of the brain. Recently, genetically encoded proteins make it possible to mediate and monitor the brain function from the molecular level to networks with cell specificity under multi-modal neuroimaging platform. Specific brain cells can be activated and the activity signal can be monitored inside the MRI-scanner with fiber optic-mediated signal detection strategies. However, it remains challenging to precisely target the brain cells in specific brain nuclei of animal brains (only a few hundred micron size). The common way is to use the animal brain atlas (e.g. Paxinos rat brain atlas) to find the 3D coordinates based on a control point (zero point), which is defined by the bregma (the anatomical point on the skull at which the coronal suture is intersected perpendicularly by the sagittal suture). The physical position of the bregma point on the skull varies largely across animals with over a few hundred micron, which contributes to the key variation for most of the animal brain nuclei surgical procedures.

The above mentioned animal brain studies are conducted on small animals like rodents e.g. rats. Typical MR scanners used for human subjects (with bore size >60 cm) are however unsuitable for imaging small animal models, since it has been found to be difficult to achieve a reasonable spatial resolution at an acceptable signal-to-noise ratio with such scanners. Thus, special "small-bore" animal high magnetic field MRI-scanners are typically used.

So far, no MRI-compatible, automatic robotic control, real-time guiding system exists, which further may be applied in special "small-bore" animal-MRI-scanners. However, there are clearly scientific needs for such a device. Especially during the new era of Human Brain Project and BRAIN INITIATIVE from the European Union and the USA, there will be tremendous opportunities to carry on animal experiments under the precise brain targeting scheme to study brain function from molecules to networks.

Object of the invention is therefore to provide a positioning system for an imaging device that overcomes the above-mentioned disadvantages.

SUMMARY

The problem is addressed by a positioning system for an imaging device, in particular a MR imaging device to position an insertion element on or in the body of a subject, in particular an animal, wherein the imaging device comprises a bore, in which the subject is received, wherein the positioning system comprises a robot, which can be at least partially arranged in the bore of the imaging device and comprises a holding element to hold the insertion element; wherein the robot further comprises at least one actuator acting on the holding element such that an end portion of the insertion element is movable, wherein said at least one actuator is arranged with a distance D from the bore to minimize magnetic and/or electromagnetic interferences between the imaging device and the at least one actuator and said first actuator is coupled to the holding element in a form-fit- and/or a force-fit-manner.

Due to the arrangement of the at least one actuator at a distance D from the imaging device or the bore respectively magnetic and/or electromagnetic interferences are minimized. Such interferences or influences may be the magnetic field or the stray magnetic field of an MRI-device influencing the at least one actuator. Such an influence may be a force on ferromagnetic components of the actuator. Typically, the magnetic fields used in such imaging devices are in the range of several Tesla. Magnetic fields of such a strength impede the functionality or would even destroy conventional actuators. Further, due to the acting forces in the magnetic field the ferromagnetic parts may be accelerated towards the imaging device, which leads to a potential risk of injuries for the subject and or personal operating the device. Further, such interferences could also be influences on the imaging device, in particular the RF coils of the imager. Electromagnetic interferences originating from the actuators could for example create image artifacts. Due to the positioning of the actuators at a distance D, it is possible to use conventional actuators. There is no need for costly special (MRI-) compatible actuators. Due to the form-fit- and/or a force-fit-coupling between the holding element and the actuator, a straightforward and inexpensive solution for the transmission of the force between actuator and holding element is presented. The subjects are preferably small animals like rodents, e.g. rats. However it is also possible to apply the positioning system on other animals like monkeys or even on humans.

Advantageously the imaging device is a fMRI-device comprising an MRI-scanner, using a magnetic field preferably in the range of 3 T to 21 T, more preferably in the range of 7 T to 14 T, and a bore diameter of preferably in the range of 50 cm to 6 cm, more preferably 12 cm. Preferably the insertion element can be a fiber-optic for optogenetic stimulation and fluorescent recording from endogenous/exogenous biosensors of metabolites of the subject brain, an electrode for recording electrophysiological or electrochemical signal, and an implantable pump/needle for direct drug delivery to treat tumor or other diseases.

Obviously the distance D depends on the magnetic field the imaging device uses. In the case of small animals, typically a magnetic field in the range of 7 T to 14 T is preferred. For a magnetic field of 14 T (without active shielding) the distance D is 4.7 meters. For conventional MRI-scanners, e.g. 9.4 T or 11.7 T, the distance D is shortened to less than 1.5 meters since the active shielding. Generally, the distance D is measured from the center of the bore.

Preferably the at least one actuator is a step motor such as a brushless DC electric motor. A full rotation of such an electric motor is divided into a number of equal steps, wherein the motor-position may be controlled and held. Such stepper motors may be permanent magnet step-, hybrid synchronous step- or variable reluctance step-motors. However, the use of any other type of actuator is equally conceivable. In particular the use of a piezo driven motor may be conceivable. By the use of a piezo-motor the distance D may be further decreased, since a piezo-motor is less susceptible to magnetic interferences.

Advantageously the bore has a longitudinal expansion along an X-axis and further expands along a Z-axis and a Y-axis, wherein said X-axis, Y-axis and Z-axis are orthogonal to each other. Preferably at least the end portion of the insertion element has a longitudinal extension along an A-axis, wherein the axis A and the Z-axis form an angle $\alpha$, which is in the range between 0° and ±90°, preferably in the range between 0° and ±45°.

According to a preferred embodiment the robot comprises a head part, a first and a second drive mechanism. Preferably a first actuator acts on the holding element via the first drive mechanism such that the end portion of the insertion element is linearly movable along the A-axis. It is further preferred that a second actuator acts on the holding element via the second drive mechanism such that the end portion of the insertion element can be pivoted about a pivot axis B, wherein by said pivoting-motion the angle $\alpha$, is adjusted. By said linear motion the end portion of the insertion element, for example the tip of a fiber, may therefore be inserted into the brain tissue through a hole in the skull of the subject. The pivoting-motion offers a convenient tool to insert the insertion element at a specific angle, whereby a specific adjustment to the target element is possible. Further a particular trajectory of the insertion path is executable.

According to a preferred embodiment, the first drive mechanism comprises a first pulley, which is connected to the first actuator by a first belt. Preferably the first drive mechanism further comprises a shaft, which is received in a central hub portion of the first pulley and connects the first pulley and a converting element, on which the holding element is mounted. Preferably the converting element converts a rotational motion of the first pulley into a linear motion of the holding element along the A-axis. Preferably the holding element, the first pulley, the shaft and the converting element are components of the head part.

Thus, according to this preferred embodiment the coupling of the first actuator to the holding element in a form-fit- and/or a force-fit-manner is achieved by a belt drive. Advantageously the first belt is looped over the first pulley and a pulley connected to the first actuator. Hereby, different embodiments known in the state of the art are conceivable for example a normal belt drive or a crossed belt. Conceivable belts are flat belts. V-belts, multi groove belts or the like. Further, the first belt may be connected to the first pulley in a force-fit-manner. Preferably the connection between the first belt and the first pulley is in a form-fit-manner. Such belts are called trimming-, toothed-, notch-, cog-, synchronous- or positive-transfer-belts. These belts have teeth that fit into a matching toothed pulley. When correctly tensioned, they have no slippage, and run at constant speed. By using the first drive mechanism according to this embodiment, a high precision and accuracy can be achieved at very low costs. The step size of the first actuator can be transferred to the converting element through the belt in an efficient manner. Further the drive mechanism can be easily adjusted to the space available in the scanner room, by altering the belt length.

According to a further embodiment, the converting element comprises a disc-like element with a first surface on which a first guiding element is arranged. Preferably the holding element comprises at least one, preferably at least three second guiding element(s), which engage(s) the first guiding element.

Advantageously the first guiding element has a continuous course, which originates in, or in the proximity of a center of the disc-like element, wherein the continuous course evolves in form of a spiral to an edge of the disc-like element. Preferably the spiral is described by a polar equation of $r=a*\theta$, wherein r is the radial distance, $\theta$ is the polar angle and a is a constant >0. Such a spiral is called an Archimedean spiral. The Archimedean spiral has the property that any ray from the origin intersects successive turnings of the spiral in points with a constant separation distance (equal to $2\pi a$ if $\theta$ is measured in radians).

The first and the second guiding element are preferably designed as a projection. Thus, the first guiding element could be continuous projection on the first surface of the disc-like element. The second guiding element(s) could be (a) projection(s) or (a) pin(s), which engage(s) and (is) are guided by the first guiding element in form of a spiral. The projection could be formed on the holding element. It is also conceivable that the second guiding element(s) is (are) (a) pin(s) which (is) are arranged in (a) bore(s) of the holding element. The projection fits preferably in the space between two points of the projecting spiral without play. Hereby an accurate guiding is ensured. It is also conceivable that the first guiding element is a slit, a groove or the like, arranged on the first surface of the disc-like element. The second guiding element in form of a projection may then engage in such a structure preferably without play.

A rotation of the disc-like element and the Archimedean spiral respectively drives the holding element due to the engagement of the second guiding element(s) along the A-axis. Due to different parameters, e.g. said separation distance, of the Archimedean spiral and precision of the step motors, different precision can be achieved. Preferably one round of the actuator (step-motor) causes one rotation round of the Archimedean spiral. In a preferred embodiment one round of the Archimedean spiral displaces the holding element by 2 mm and the smallest step-size of the holding element along the A-axis is 10 μm. Thus, it is possible to accurately and precisely target the deep brain nuclei with a simple and inexpensive mechanism.

According to a further preferred embodiment the second drive mechanism comprises a second pulley, which is connected to the second actuator by a second belt. The second drive mechanism preferably comprises further a cup-like element, which is rigidly connected to the second pulley. Advantageously the cup-like element comprises a receiving element, which extends along the A-axis and receives the holding element. Preferably the cup-like element engages the holding element such that a rotational motion of the cup-like element causes a pivoting-motion of the holding element around the B-axis. Preferably the second pulley and the cup-like element are a component of the head part of the robot.

It is further advantageous that the receiving element allows the motion of the holding element along the A-axis. The receiving element is preferably designed as a slit or a groove in which the holding element is received and guided. It is also conceivable that the receiving element is designed as a projection on the cup-like element which extends along the A-axis. Accordingly the holding element would comprise a structure like a groove in which the projection engages. Thus, according to this preferred embodiment the coupling of the second actuator to the holding element in a form-fit- and/or a force-fit-manner is achieved by a belt drive. Advantageously the second belt is looped over the second pulley and a pulley connected to the second actuator. Hereby, different embodiments known in the art are conceivable, for example a normal belt drive or a crossed belt. Conceivable belts are flat belts. V-belts, multi groove belts or the like. Further, the second belt may be connected to the first pulley in a force-fit-manner. Preferably the connection between the second belt and the second pulley is in a form-fit-manner. Such belts are called trimming-, toothed-, notch-, cog-, synchronous- or positive-transfer-belts. These belts have teeth that fit into a matching toothed pulley. When correctly tensioned, they have no slippage, and run at constant speed. By using the second drive mechanism according to this embodiment, a high precision and accuracy can be achieved at very low costs. The step size of the second actuator can be transferred to the converting element through the belt in an efficient manner. Further, the drive mechanism can be easily adjusted to the space available in the scanner room by altering the belt length.

Preferably the shaft projects through the center of the second pulley. However, there is no connection between the shaft and the second pulley, which would transmit rotational motion between the second pulley and the shaft or vice versa. The minimal friction forces between the shaft and the second pulley are negligible. Thus, the rotational motions of the first pulley and the second pulley are effectively decoupled from each other. It is further favorable that the pivoting-motion of second pulley and the cup like element is blocked by the second actuator when the first actuator drives the holding element via the first drive mechanism. In this way the angle α is unchanged and the motion of the holding element is guided by the receiving element.

By using belt drives in the first and second drive mechanisms, not only the problem of the undesired interferences is addressed, also the physical limitation of in-bore access and the limited workspace in the bore (12 cm for small animal MRI's) can be advantageously addressed, since the head part of the robot can be designed relatively small.

In a further preferred embodiment, the head part of the robot is connected to a holding rod via a connection element. Preferably the robot further comprises a third actuator which acts on the holding rod via a third drive mechanism, such that the head part of the robot can be moved along the Y-axis. It is further preferred that the robot comprises a fourth actuator, which acts on the holding rod via a fourth drive mechanism, such that the head part of the robot can be moved along the X-axis. The displacement of the head part of the robot along the X- and Y-axis allows a positioning of the insertion element over the inserting point, e.g. a hole in the skull of the subject.

According to a preferred embodiment the third drive mechanism comprises a third pulley, which is connected to the third actuator by a third belt. Preferably the third pulley is rigidly connected to a threaded spindle on which a nut is arranged. Advantageously, the nut is connected to the holding rod of the robot. It is preferred that the threaded spindle is arranged perpendicularly to the holding rod. Preferably a rotation of the third pulley causes a rotation of the threaded spindle and a movement of the nut and the holding rod along the Y-axis. It is further conceivable that the third drive mechanism comprises further threaded spindles with accompanied nuts. These spindles may advantageously be arranged along the length of the holding rod at equal distances. Each spindle is driven by a belt which is connected to a pulley arranged on a spindle closer to the third actuator. In this way a chain-like drive is obtained.

Thus, according to this preferred embodiment the coupling of the third actuator to the holding element, a form-fit- and/or a force-fit-manner is achieved by a belt drive. Advantageously the third belt is looped over the third pulley and a pulley connected to the third actuator. Hereby, different embodiments known in the art are conceivable for example a normal belt drive or a crossed belt. Conceivable belts are flat belts. V-belts, multi groove belts or the like. Further, the third belt may be connected to the third pulley in a force-fit-manner. Preferably the connection between the third belt and the third pulley is in a form-fit-manner. Such belts are called trimming-, toothed-, notch-, cog-, synchronous- or positive-transfer-belts. These belts have teeth that fit into a matching toothed pulley. When correctly tensioned, they have no slippage, and run at constant speed. By using the third drive mechanism according to this embodiment, a high precision and accuracy can be achieved at very low costs. The step size of the third actuator can be transferred to the converting element through the belt in an efficient manner. Further, the drive mechanism can be easily adjusted to the space available in the scanner room by altering the belt length.

According to a preferred embodiment, the third drive mechanism acts additionally on a first translation stage. Advantageously, the first actuator, the pulley connected to the first actuator, the second actuator, the pulley connected to the second actuator and the holding are mounted on the first translation stage. Preferably said translation along the Y-axis, driven by the third pulley and the third belt, of the one or more nuts, connected to the holding rod, is accompanied by a translation of the first translation stage along the Y-axis. It is preferred that the translation distance of the first translation stage and the one or more nuts, connected to the holding rod are the same, to ensure an accurate displacement without bending the holding rod or causing tension in the holding rod. The third drive mechanism advantageously further comprises a gear, a threaded spindle or the like, which is driven by the third actuator, and is also arranged at a distance D from the bore.

According to a further preferred embodiment, the fourth drive mechanism acts on a second translation stage. Advantageously, on second translation stage the first translation stage and the third actuator are arranged. Preferably, a translation of the second translation stage along the X-axis results in a translation of the first translation stage, its elements mounted on it and the third actuator as a whole along the X-axis. The fourth drive mechanism advantageously further comprises a gear, a threaded spindle or the like, which is driven by the fourth actuator and which is also arranged at a distance D from the bore.

In addition, it is advantageous that the positioning system comprises a platform, on which the robot (5) is arranged. Preferably the subject is suspended and/or held at a head part of the platform, which can be arranged in the bore of the imaging device. Preferably the first, second, third and fourth actuators are arranged at the foot part of the platform (40). Preferably the threaded spindle(s) is (are) arranged on (a) holder(s) connected to the platform.

Advantageously, the robot and the platform mainly consist of MRI-compatible materials. Preferably such materials are nonmagnetic, dielectric materials, plastics, rubbers, or ceramics. It is also preferable that the components of the robot may consist of minimal amounts of brass or anodized aluminum to avoid deterioration of magnetic field homogeneity. The holding rod preferably is constructed from carbon fiber. The advantage of the carbon fiber is its very light weight, which allows the use of conventional step motors with relative small set sizes. Although the conductivity of carbon fiber could get a certain eddy current during the MR imaging because of the MR gradient shift, it is negligible for the animal fMRI studies. For human safety issue, however, it may be better to replace all carbon fiber material to fiber-glass-based material.

According to a preferred embodiment the positioning system comprises at least one, preferably at least two MRI-compatible camera(s), which is (are) mounted on the head part of the platform.

Preferably the positioning system further comprises a navigation unit, which advantageously comprises a control unit. Preferably the control unit controls the motion of the first, second, third and fourth actuator. It is advantageous that the navigation unit further comprises an image processing unit which processes real time images of the imaging device and/or the at least one camera in the bore.

The object is also addressed by a method to position an insertion element using a positioning system according to any one of the preceding embodiments in a MR imaging device:

a. Lowering the insertion element by the robot to a first position on the subject or close to the subject;

b. Acquiring a 3D-MRI image and process the image via the image processing unit to identify the location of subject, as well as the position of insertion element;

c. Calculation of the coordinates of the target point and the insertion element and calculation of an optimized movement trajectory for the insertion element by the control unit;

d. Monitoring movement trajectory by real-time MRI image via the image processing unit.

Advantageously, the navigation unit allows an operator to visualize the (MRI-) image form the imaging device. A target and an entry point for the insertion element is defined by a brain atlas and a 3D MRI-image by a control algorithm of the control unit. Preferably, two cameras are positioned to obtain visual guidance of the insertion, e.g. a brain intervention. Preferably camera-based visual signals are presented by the navigation unit. Thus, the operator can monitor the real time situation inside the scanner. Alternatively the operator could also manually adjust the target and an entry point.

The method may be particularly adjusted to automatically control a fiber/electrode (insertion element) insertion into the brain of a small animal. Preferably the following steps may be performed before step a)

Applying a craniotomy on the animal skull;

Fixing the animal on the head part of the platform with RF coil attached on the animal head;

Covering the skull with a circular transparent agarose gel with 1 cm diameter and 2 mm thickness;

Positioning the head part of the robot above the animal skull;

Setting at least two MRI-compatible cameras (≥2) to directly visualize the craniotomy and fiber/electrode tip;

Placing the head part of the platform and the head part of the robot in the bore of the MRI-scanner.

Step a) is adjusted such that the fiber/electrode is lowered for 1 mm to insert into the agarose gel.

Step b) is adjusted such that a 3D MRI image is acquired to identify the location of animal brain, as well as the position of the fiber/electrode tip in the agarose gel.

Step c) is adjusted such that the coordinates of the interested brain nuclei and the fiber/electrode tip will be calculated from the 3D MRI images and that the optimized movement trajectory of the fiber/electrode is calculated.

Step d) is adjusted such that the real-time MRI image can monitor the location of the fiber after the insertion into the animal brain.

Further, the MRI-compatible cameras can be used to directly visualize the movement of the fiber/electrode tips outside the animal brain.

Thus, an advantageous multiple degree-of-freedom robotic controlling system to target brain nuclei or specific brain cells in the brain inside the high field (14.1 T) MRI-scanner is provided. A MRI-compatible positioning system provides feasible targeting accuracy, high temporal and spatial resolution by using MRI images as feedback to guide the brain intervention. Meanwhile, a MRI-compatible camera-monitored insertion trajectory is optimized in order to investigate the effectiveness, safety and feasibility of deep brain nuclei targeting for translational application. The positioning system provides:

A fully motor-based automatic system using the MRI images to guide the brain intervention;

A special design for animal brain surgeries, which is also possible to be expanded to the whole animal body in vivo targeting inside the MRI-scanner;

Compatibility with the 14 T high magnetic field of the MRI-scanners, which could also be even pushed to 17 T;

Accommodation of the space limit of the high field MRI-scanners, The positioning system is even applicable to 8 cm bores;

Providing a fully implementable system with build-in camera and RF surface coil to allow direct measurement of MRI images and position of electrode/fiber optic/injection needle tips;

Providing a 50-100 micron resolution to target the region of interests;

Providing an individual animal specificity with more precise targeting strategy than only based on the atlas.

The multimodal neuroimaging methodologies on animal models are crucial for better understanding brain function. The neuron-glia-vessel (NGV) network is one of the most challenging areas given the multifaceted requirements of signal acquisition from the brain. The combination of fMRI with optogenetic stimulation of genetically defined cells in animal models has enabled scientists to study the causality between the activation of specific neuronal populations and the hemodynamic signal, such as the blood-oxygen-level-dependent (BOLD) fMRI signal. Simultaneous BOLD fMRI and fiber-optic recording of fluorescent calcium signal can help clarify the cellular contributions to neurovascular coupling in different brain regions of healthy and diseased animal models. The hereby solved key challenge of the fiber optic-mediated multimodal fMRI methodologies is how to locate the fiber tip accurately and to precisely target the deep brain nuclei, mostly the requirement of precision is only several hundreds of microns.

Further advantages, aims and properties of the present invention will be described by way of the appended drawings and the following description.

DETAILED DESCRIPTION

Figure 1:
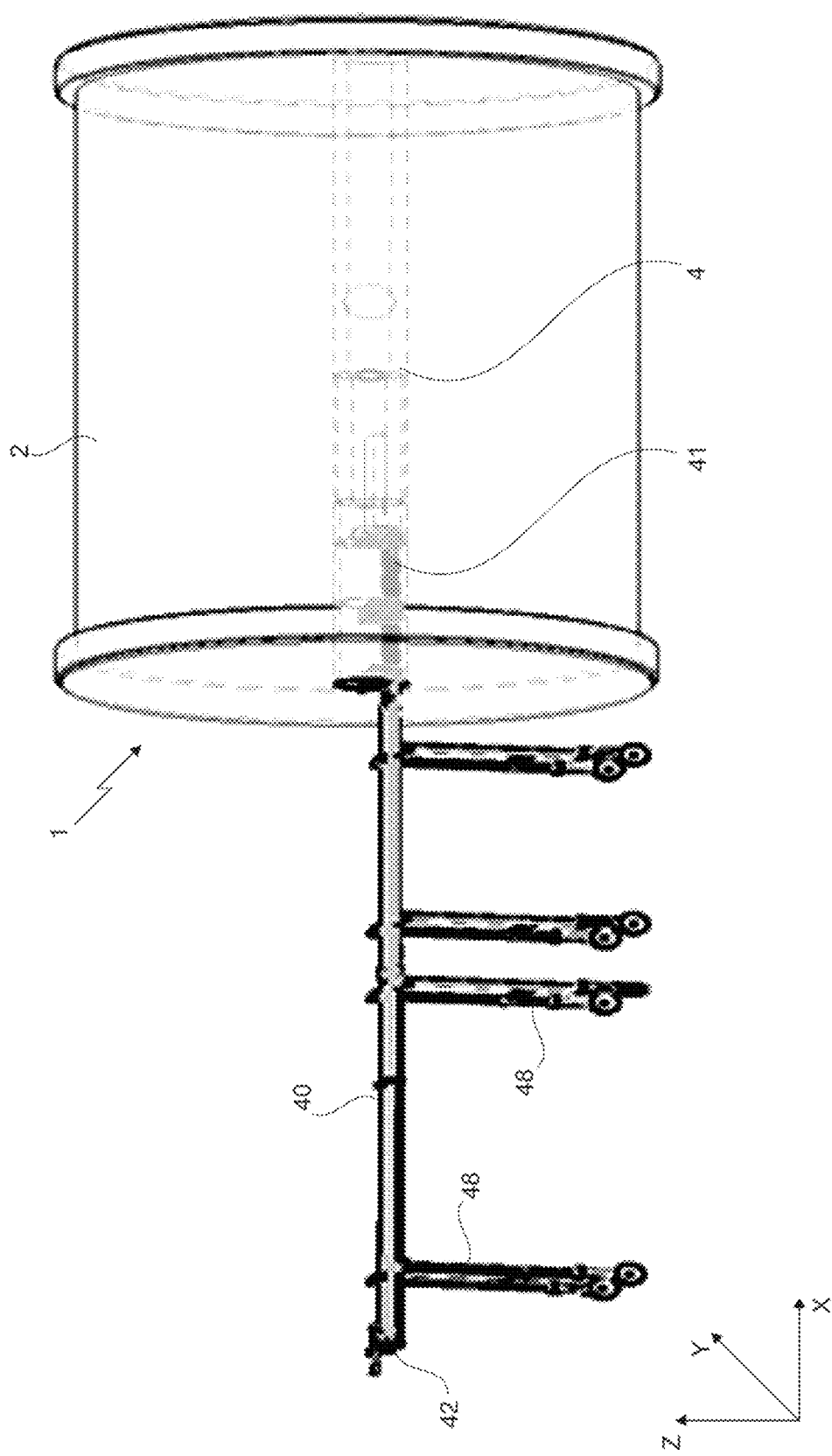
FIG. 1 shows the platform with the robot arranged in the imaging device according to one embodiment.

Without limiting the generality, in the following embodiments a MRI-(Magnetic resonance imaging) device is assumed as imaging device. Such an imaging device (2) is a fMRI-device comprising an MRI-scanner, using a magnetic field preferably in the range of ca. 3 T to ca. 21 T more preferably in the range of ca. 7 T to ca. 14 T, and a bore diameter of preferably in the range of 50 cm to 6 cm, more preferably 12 cm, wherein the insertion element can be a fiber-optic for optogenetic stimulation and fluorescent recording from endogenous/exogenous biosensors of metabolites of the subject brain, an electrode for recording electrophysiological or electrochemical signal, and an implantable pump/needle for direct drug delivery to treat tumor or other diseases.

FIGS. 1 to 8 display a positioning system (1) for an imaging device (2), in particular a MR imaging device, to position an insertion element (3) on or in the body of a subject, in particular an animal, wherein the imaging device (2) comprises a bore (4), in which the subject is received, wherein the positioning system (1) comprises a robot (5), which can be at least partially arranged in the bore (4) of the imaging device (2) and comprises a holding element (7) to hold the insertion element (3); wherein the robot (5) further comprises at least one actuator (8, 9, 10, 11), acting on the holding element such that an end portion (3a) of the insertion element (3) is movable, wherein said at least one actuator (8, 9, 10, 11) is arranged with a distance D from the bore to minimize magnetic and/or electromagnetic interferences between the imaging device (2) and the at least one actuator (8, 9, 10, 11) and said first actuator (8, 9, 10, 11) is coupled to the holding element (3) in a form-fit- and/or a force-fit-manner.

FIG. 1 shows a MRI-scanner, typically located in a scanner room, and a platform (40), on which the robot (5) is arranged. The bore (4) of the imaging device (2) has a longitudinal expansion along an X-axis and further expands along a Z-axis and a Y-axis, wherein said X-axis, Y-axis and Z-axis are orthogonal to each other. The platform (40) has a longitudinal expansion along the X-axis of at least the distance D and a width which expands along the Y-axis. Further, the platform is mounted on a support device (48) which is equipped with several wheels and is partially arranged in the bore (4) of the imaging device (2).

The robot (5) further comprises a first (12) and a second drive mechanism (13) and a first (8) and a second actuator (9). These components are depicted in FIGS. 2 to 6. The first actuator (8) acts on the holding element (7) via the first drive mechanism (12) such that the end portion (3a) of the insertion element (3) is linearly movable along the A-axis. The second actuator (9) acts on the holding element (7) via the second drive mechanism (13) such that the end portion (3a) of the insertion element (3) can be pivoted about a pivot axis B, wherein by said pivoting-motion the angle α, is adjusted. The first (8) and the second actuator (9) are mounted at a foot part (42) of the platform (40) wherein the foot part (42) is arranged with a distance D from the bore (4) to minimize magnetic and/or electromagnetic interferences between the imaging device (2) and the actuators (8, 9).

The holding element (7) comprises a body (7a) of an essentially rectangular shape which extends along the A-axis. The bores for the second guiding elements (24) in form of pins are arranged in row, placed in the center of the rectangular body (24a). On the body (7a) a gripping portion (7b) is arranged, by which the insertion element (3) is fastened. Further, the body (24a) comprises two lateral grooves (54a, 54b).

Figure 2A:
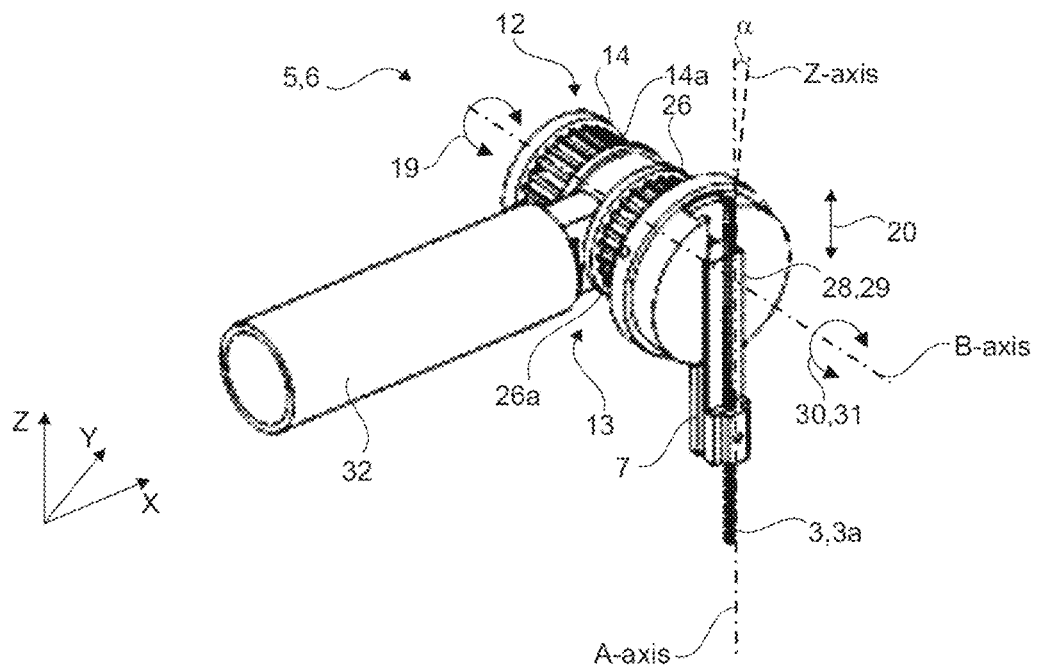
FIG. 2A shows the head part of the robot according to one embodiment.
Figure 2B:
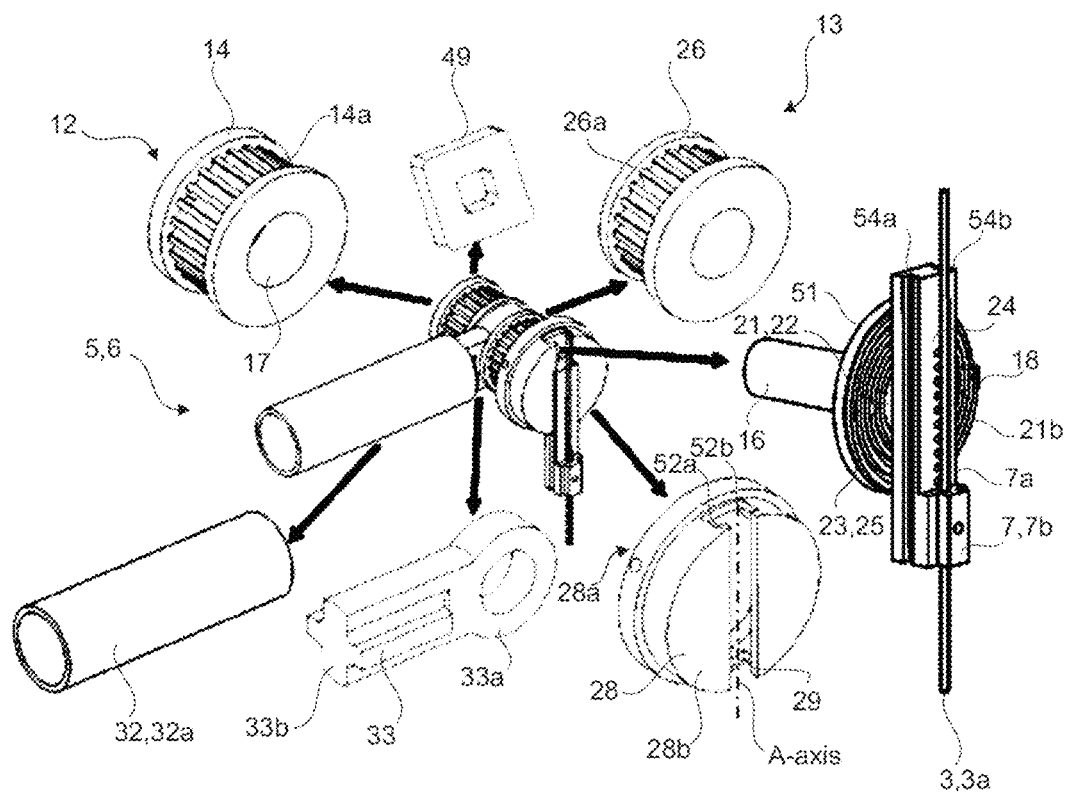
FIG. 2B shows the head part of the robot and its components according to one embodiment in an exploded view.

The FIGS. 2A and 2B display a head part (6) of the robot (5), wherein the individual components of the head part (6) are shown in FIG. 2B in an exploded view. The components of the head part (6) are the holding element (7), a first pulley (14), a second pulley (26), a shaft (16) which is rigidly connected to a converting element (18), a cup-like element (28), a connection element (33), which connects the head part (6) to a holding rod (32), and a fixing element (49).

Figure 5:
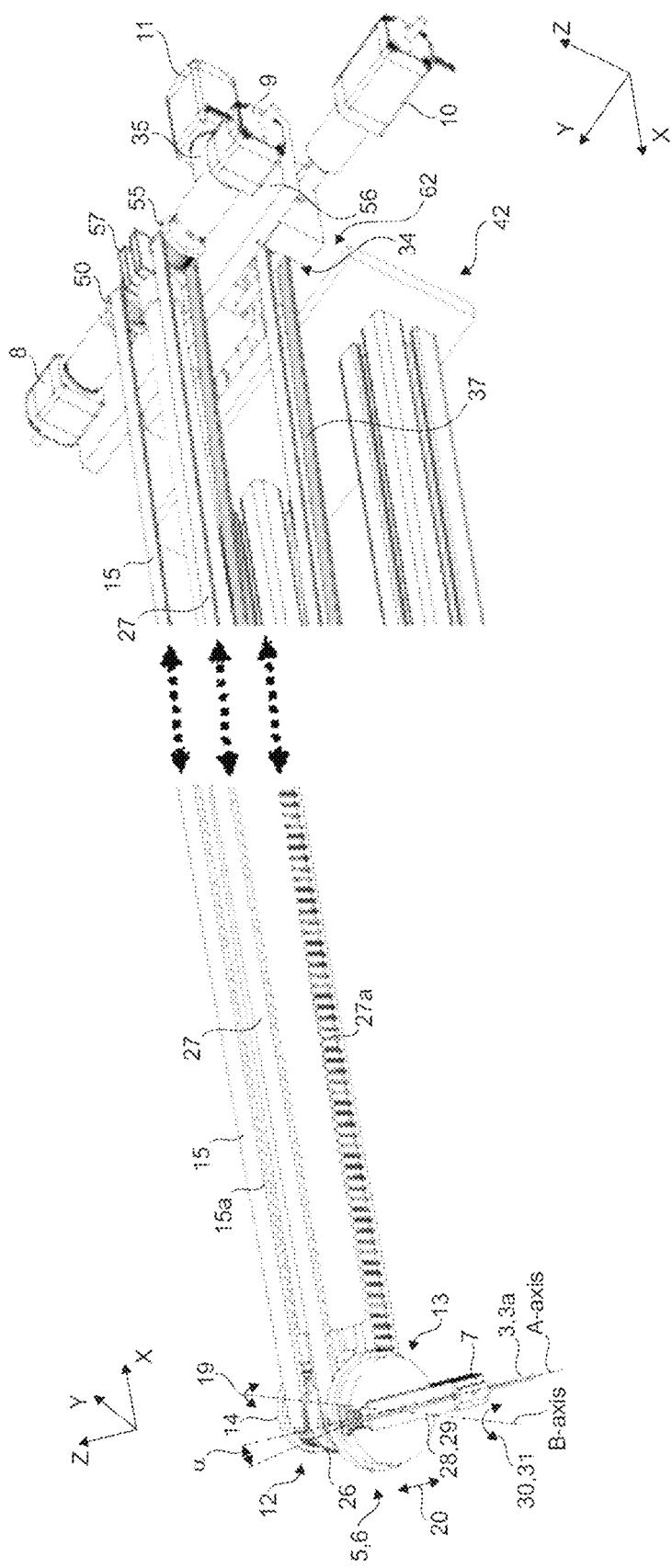
FIG. 5 shows the robot according to one embodiment.

The first drive mechanism (12) comprises the first pulley (14), which is connected to the first actuator (8) by a first belt (15), the shaft (16), which is received in a central hub portion (17) of the first pulley (14) and connects the first pulley (14), and the converting element (18), on which the holding element (7) is mounted. The converting element (18) converts a rotational motion (19) of the first pulley (14) into a linear motion (20) of the holding element (7) along the A-axis. Thus, the coupling of the first actuator (8) to the holding element (7) in a form-fit- and/or a force-fit-manner is achieved by such a belt drive. The first belt (15) is looped over the first pulley (14) and a pulley (50) connected to the first actuator (8). FIG. 5 displays this connection between the first pulley (14) and the pulley (50) connected to the first actuator (8) by the first belt (15). The first belt (15) is a toothed belt having teeth (15a) that fit into matching teeth (14a) of the first pulley (14) and teeth of the pulley (50) connected to the first actuator (8). By such a design, slippage of the belt is avoided.

The shaft (16) is rigidly connected to the central hub portion (17) of the first pulley (14) and the converting element (18). The rotational motion of the first pulley (14) is therefore transmitted by the shaft (16) to the converting element (18).

The converting element (18) comprises a disc-like element (21) with a first surface (22) on which a first guiding element (23) is arranged. The disc-like element has a circular form with a center (21a) and an edge (21b). The shaft is rigidly connected to a second surface (51) opposite to the first surface (22).

The first guiding element (23) has a continuous course, which originates in, or in the proximity of the center (21a) of the disc-like element (21), wherein the continuous course evolves in form of a spiral (25) to the edge (21b) of the disc-like element (21). The spiral (25) is described by a polar equation of $r=a*\theta$, wherein r is the radial distance, $\theta$ is the polar angle and a is a constant >0. Such a spiral (25) is called an Archimedean spiral. The Archimedean spiral has the property that any ray from the center (21a) intersects successive turnings of the spiral (25) in points with a constant separation distance (equal to $2\pi*a$, $\theta$ is measured in radians). The first guiding element (23) in the form of a spiral (25) is designed as a projection projecting from the first surface (22).

Figure 3A:
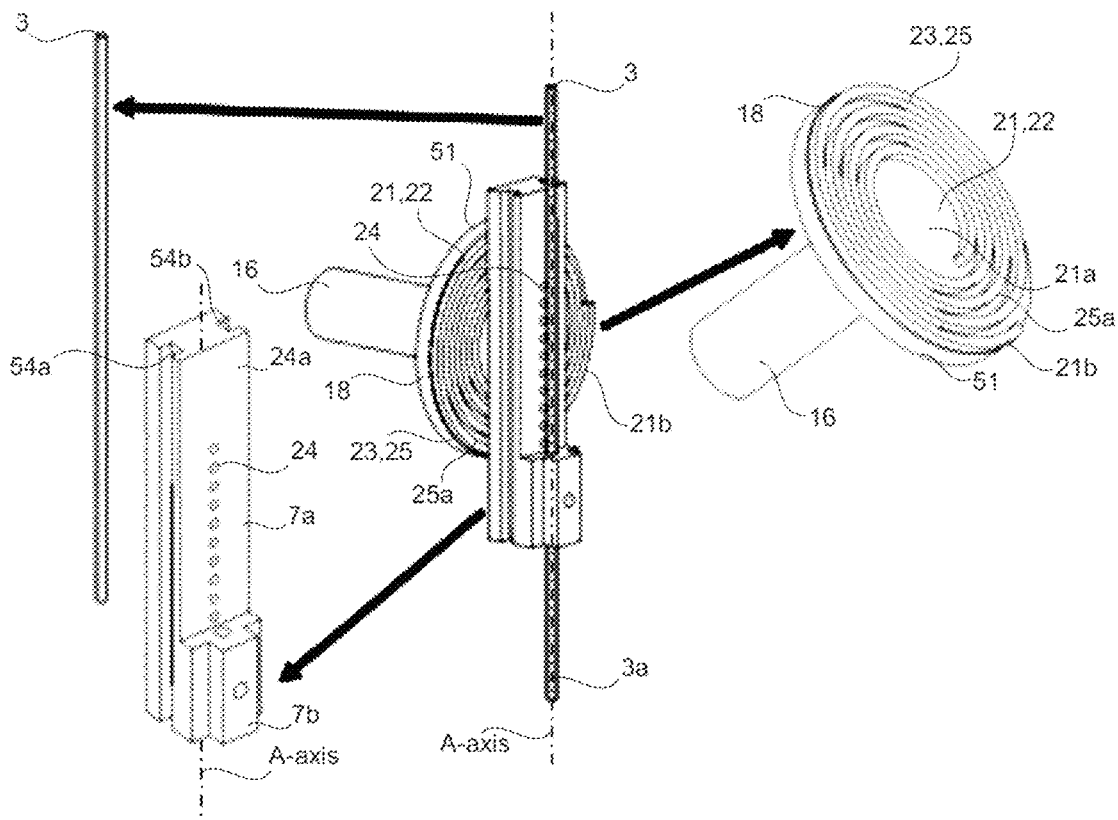
FIG. 3A shows the converting element and the holding element according to one embodiment.
Figure 3B:
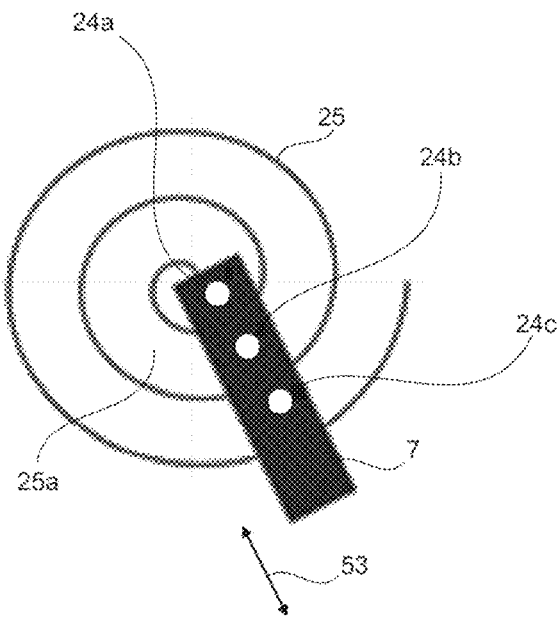
FIG. 3B shows schematically the principle of the converting element.

The holding element (7) comprises a plurality of second guiding elements (24), which engage the first guiding element (23). The second guiding elements (24) are in form of a projection or a pin which is either formed directly on the holding element (7) or rigidly arranged in bores of the holding element (7). The second guiding elements (24) in form of pins fit in the space (25a) between two opposing points of the projecting spiral (25), preferably without play. FIG. 3B displays the principle of the drive using an Archimedean spiral. The spiral (25) and the holding element (7) with three exemplary second guiding elements (24): second guiding element one (24a), second guiding element two (24b) and second guiding element three (24c) are shown in this FIG. 3B. The distance between second guiding element one (24a) and second guiding element two (24b) is the same as the distance between second guiding element two (24b) and second guiding element three (24c). A rotation of the Archimedean spiral (25) will drive the holding element (7) up or down along the direction of arrow (53).

In this embodiment one round of the Archimedean spiral (25) displaces the holding element (7) by 2 mm and the smallest step-size of the holding element (7) along the A-axis is 10 µm. Thus, it is possible to accurately and precisely target the deep brain nuclei with a simple and inexpensive mechanism.

The holding element (7) is further secured by the cup-like element (28). The cup-like element (28) is rigidly connected to the second pulley (26), encloses the disc-like element (21) and comprises a receiving element (29), which extends along the A-axis and receives the holding element (7). The disc-like element (21) is received in the inner space (28a) of the cup-like element (28) such that it may rotate freely. The holding element (7) is received in the receiving element (29) such that only the linear motion (20) along the A-axis is allowed. In this way a rotation of the holding element due to a force transmission, for example due to the friction between the disc-like element (21) and the holding element, is prevented.

The receiving element (29) is designed as a slit in the frontal part (28b) of the cup-like element (28). The slit comprises two opposing guiding projections (52a, 52b) on its edges, which project radially inwards and extend along the A-axis. Each of the guiding projections (52a, 52b) engages in a groove (54a, 54b) of the holding element (7), which also extends along the A-axis.

The second drive mechanism (13) comprises a second pulley (26), which is connected to the second actuator (9) by a second belt (27), and a cup-like element (28), which is rigidly connected to the second pulley (26). The cup-like element (28) comprises the receiving element (29), which extends along the A-axis and receives the holding element (7). The cup-like element (28) engages the holding element (7) such that a rotational motion (30) of the cup-like element (28) causes a pivoting-motion (31) of the holding element (7) around the B-axis. In particular the rotational motion of the second pulley (26) is transferred to the holding element (7) via the engagement of the guiding projections (52a, 52b) in the lateral grooves (54a, 54b) of the holding element (7). Thus, the coupling of the second actuator (9) to the holding element (7) in a form-fit- and/or a force-fit-manner is achieved by such a belt drive. The second belt (27) is looped over the second pulley (26) and a pulley (55) connected to the second actuator (9). FIG. 5 displays this connection between the second pulley (26) and the pulley (55) connected to the second actuator (9) by the second belt (27). The second belt (27) is a toothed belt having teeth (27a) that fit into matching teeth (26a) of the second pulley (26) and teeth of the pulley (55) connected to the second actuator (9). By such a design, slippage of the belt is avoided.

Once the angle α is adjusted by the pivoting-motion (31) of the holding element (7) around the B-axis, the actuator blocks any further motion. In this way an effective guidance of the linear motion (20) of the holding element (7) along the adjusted A-axis by the engagement of the guiding projections (52a, 52b) in the lateral grooves (54a, 54b) is ensured.

The shaft (16) projects through the center of the second pulley (26). However, there is no connection between the shaft (16) and the second pulley (26), which would transmit rotational motion between the second pulley (26) and the shaft (16) or vice versa. The minimal friction forces between the shaft (16) and the second pulley (26) are negligible (which is highly dependent on the material used, e.g. fiber glass or titanium with high rigidity is preferred). Thus, the rotational motions of the first pulley (14) and the second pulley (26) are effectively decoupled from each other. Additionally the shaft is fixed by a fixing element (49).

Between the first (14) and the second pulley (26) the connection element (33), which connects the head part (6) of the robot (5) to the holding rod (32), is arranged. The connection element (33) comprises a loop portion (33a) and an insertion portion (33b). The shaft (16) projects through the loop portion (33a). However, there is no connection between the shaft (16) and the loop portion (33a), which would transmit rotational motion between the second pulley (26) and the shaft (16) or vice versa. The minimal friction forces between the shaft (16) and the loop portion (33a) are negligible. The arrangement of the loop portion (33a) of the connection element (33) between the first (14) and second pulley (26) is further advantageous, since a direct contact between the pulleys (14, 26) and a transmission of rotational movement between the pulleys are avoided.

The insertion portion (33b) of the connection element (33) has a cross-like shape and is inserted in a tube-like end portion (32a) of the holding rod (32). It is also conceivable that the holding rod (32) is tubular over its full length.

The holding rod (32) extends over the distance D along the platform (40) and is supported by at least one holder (43) which is connected to the platform 40. Eventually the holding rod (32) is mounted on a first translation stage (56) at the foot part (42) of the platform (40).

Figure 4:
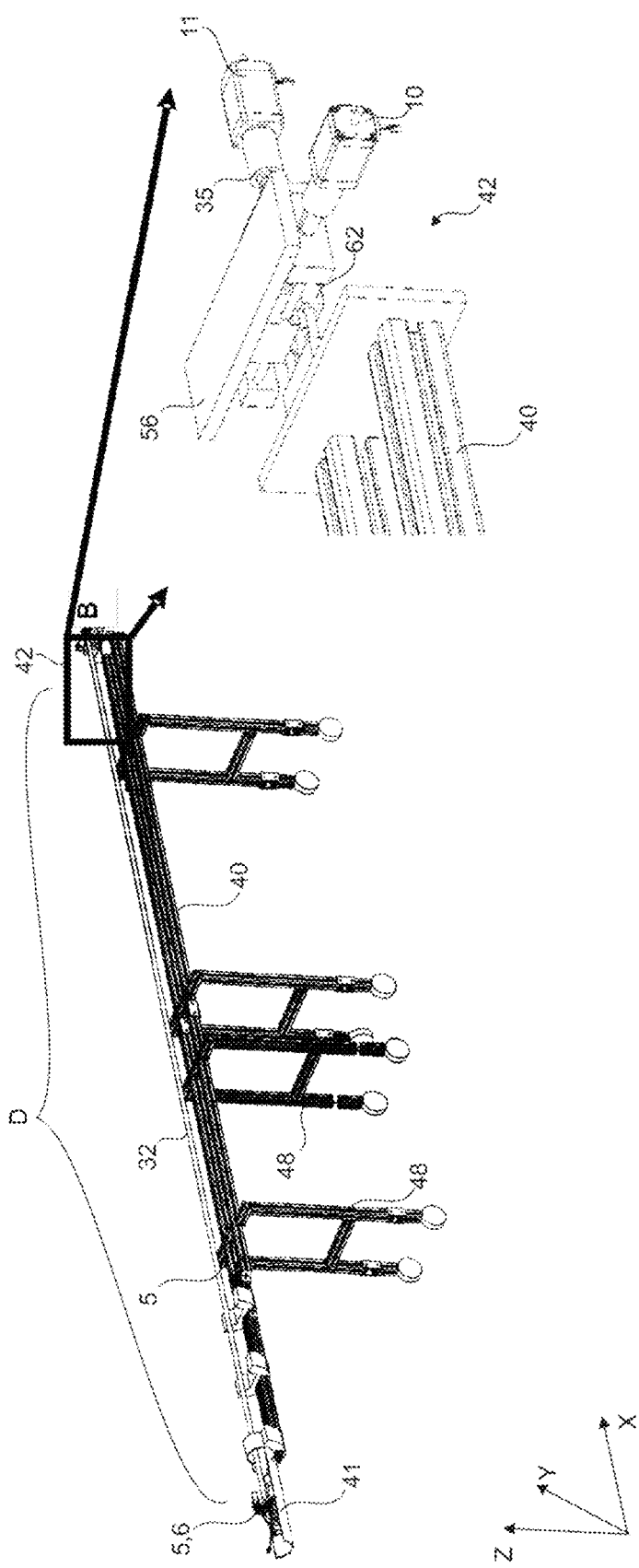
FIG. 4 shows the robot according to one embodiment mounted on the platform.
Figure 6:
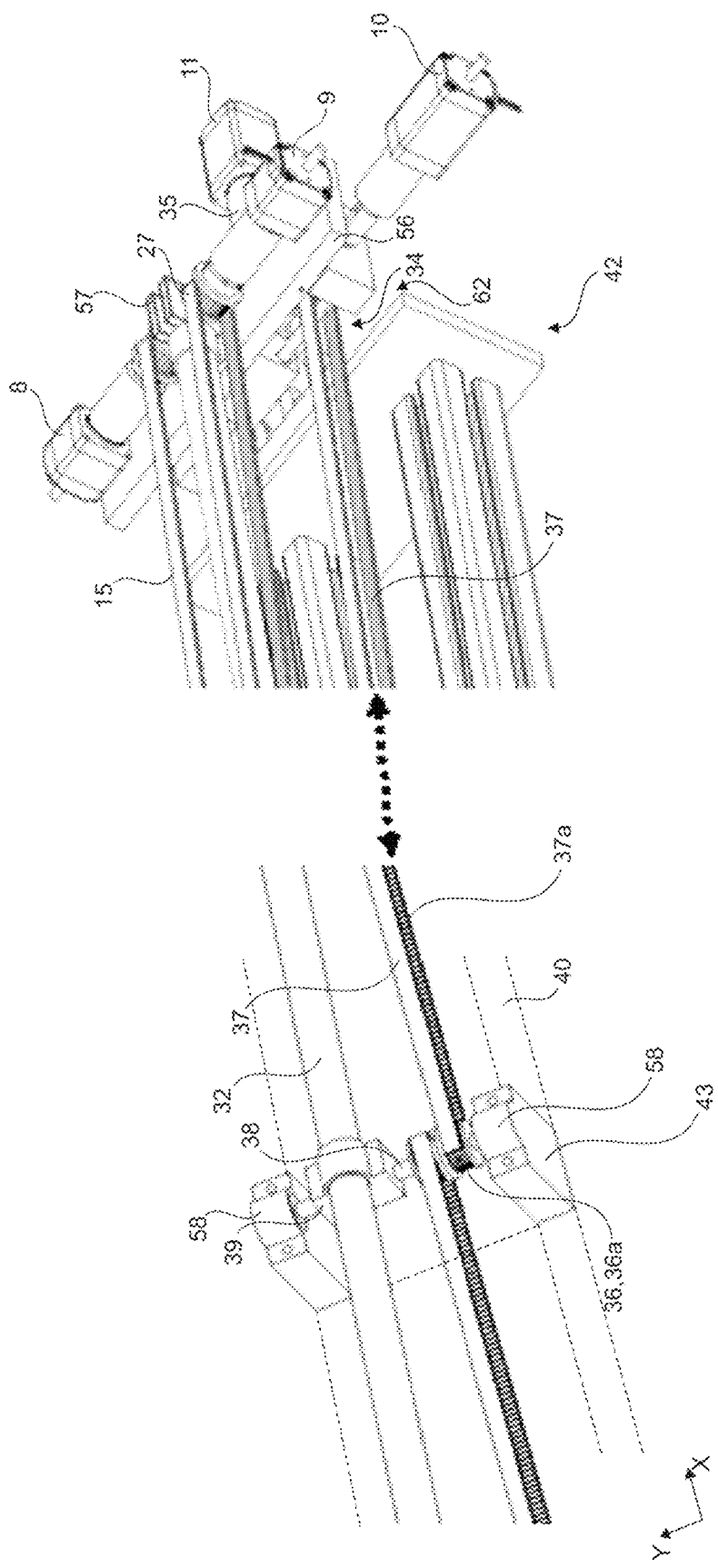
FIG. 6 shows the robot according to one embodiment.
Figure 7:
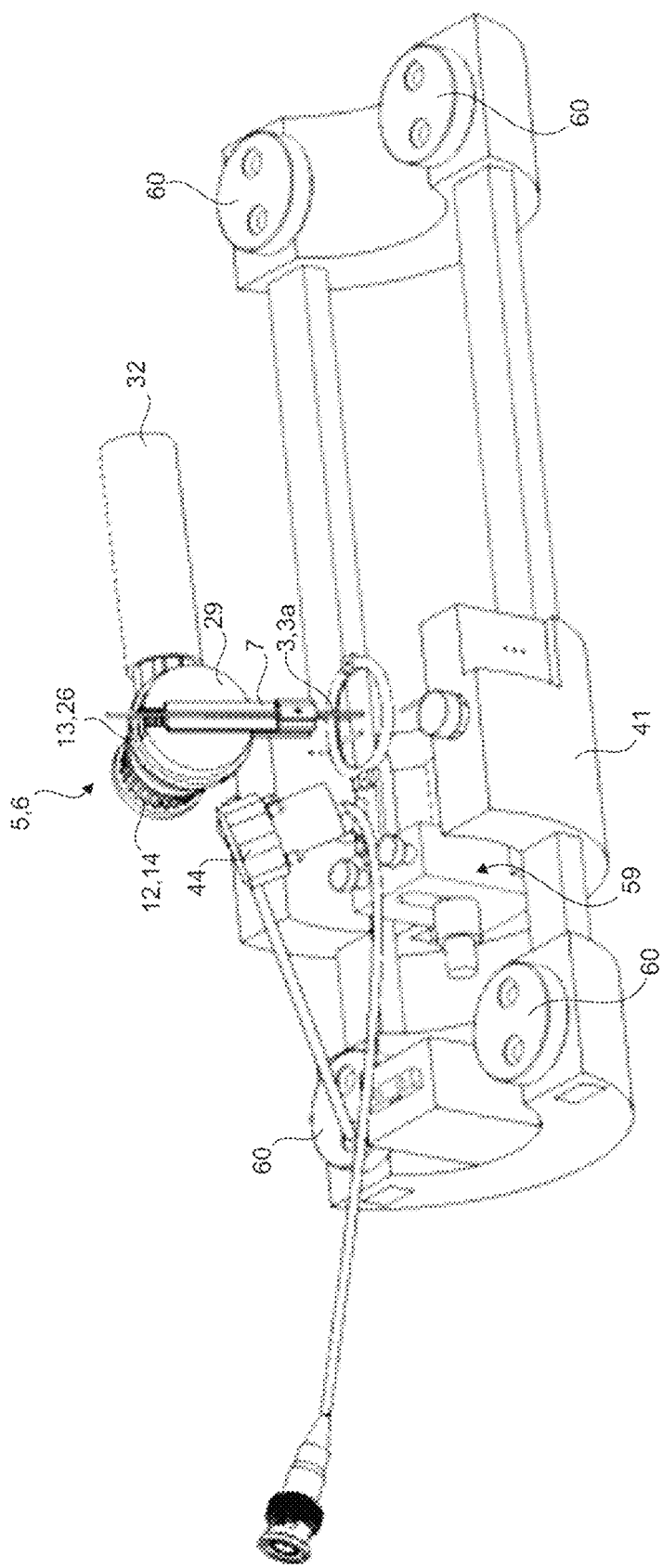
FIG. 7 shows the head part of the platform according to one embodiment.

The robot (5) further comprises a third actuator (10) which acts on the holding rod (32) via a third drive mechanism (34), such that the head part (6) of the robot (5) can be moved along the Y-axis. Additionally, the robot (5) comprises a fourth actuator (11) which acts on a holding rod (32) via a fourth drive mechanism (35), such that the head part (6) of the robot (5) can be moved along the X-axis. The third actuator (10) and the fourth actuator (11) are partially arranged underneath the first translation stage (56). The drive mechanisms (12, 13, 34, 35) are depicted in FIGS. 4 to 6.

The third drive mechanism (34) comprises a third pulley (36), which is connected to the third actuator (10) by a third belt (37). The third pulley (36) is rigidly connected to a threaded spindle (38) on which a nut (39) is arranged. The nut (39) is connected to the holding rod (32) of the robot (5). Further, the threaded spindle (38) is arranged perpendicularly to the holding rod (32). Thus, a rotation of the third pulley (36) causes a rotation of the threaded spindle (38) and a movement of the nut (39) and with it the holding rod (32) along the Y-axis. Thus, the coupling of the third actuator (10) to the holding element (7) in a form-fit- and/or a force-fit-manner is achieved by such a belt drive. The third belt (37) is looped over the third pulley (36) and a pulley (not shown in the figures) connected to the third actuator (10). The third belt (37) is a toothed belt having teeth (37a) that fit into matching teeth (36a) of the third pulley (36) and teeth of the pulley connected to the third actuator (10). By such a design, slippage of the belt is avoided. The threaded spindle (38) is mounted on the holder (43) by bearings (58).

It is further conceivable that the third drive mechanism (34) comprises further threaded spindles with accompanied nuts. These spindles may be arranged along the length of the holding rod (32) at equal distances. Each spindle is driven by a belt which is connected to a pulley arranged on spindle closer to the third actuator (10). In this way a chain-like drive is obtained.

Additionally, the third drive mechanism (34) acts on the first translation stage (56) at the foot part (42) of the platform (40). On the first translation stage (56) the holding rod (32) is mounted at the mounting element (57). Further, the first actuator (8), the pulley (50) connected to the first actuator (8), the second actuator (9) and the pulley (55) connected to the second actuator (9) are mounted on the first translation stage. A translation of the first translation stage (56) along the Y-axis results therefore in a translation of said elements as a whole mounted on it along the Y-axis. A translation along the Y-axis, driven by the third pulley (36) and the third belt (37), of the one or more nuts (39), connected to the holding rod (32), is, therefore, accompanied by a translation of the first translation stage (56) along the Y-axis. Obviously, the translation distance of the first translation stage (56) and the one or more nuts (39), connected to the holding rod (32) needs to be the same. Such a translation along the Y-direction allows an accurate displacement without bending the holding rod (32) or causing tension in the holding rod (32). Thus, the third drive mechanism (34) further comprise a gear, a threaded spindle or the like, which is driven by the third actuator (10), and is also arranged at the foot part of the platform (40) at a distance D from the bore (4).

The fourth drive mechanism (35) acts on a second translation stage (62) at the foot part (42) of the platform (40). On second translation stage (62) the first translation stage (56) and the third actuator (10) are arranged. A translation of the second translation stage (62) along the X-axis results therefore in a translation of the first translation stage (56), its elements mounted on it and the third actuator (10) as a whole along the X-axis. Thus, the fourth drive mechanism (35) can be a gear, a threaded spindle or the like, which is driven by the fourth actuator (11) and which is also arranged at the foot part of the platform (40) at a distance D from the bore (4). In FIGS. 4-6 the third (10) and fourth actuators (11) and the first (56) and second translation stage (62) are shown.

Hence, upon a command, the holding rod (32) with the whole first translation stage (56) is movable back-to-forth (along the X-axis) driven by actuator (11), and for the left-to-right motion (along the Y-axis) driven by actuator (10), the holding rod moves with the first translation stage (59) only. Such a translation along the X- and Y-axis allows an accurate displacement without bending the holding rod (32). or causing tension in the holding rod (32).

The positioning system (1) comprises at least one, preferably at least two MRI-compatible camera(s) (44), which is (are) mounted on a head part (41) of the platform (44). As already mentioned, the positioning system (1) comprises a platform (40), on which the robot (5) is arranged. The platform (40) comprises a head part (41), which can be arranged in the bore (4) of the imaging device (2), wherein the subject is suspended and/or held at this head part of the platform (40). The platform (40) with the head part (41) and the robot (5) are displayed in FIG. 4. The head part (41) is shown in detail in FIG. 7. The head part (41) comprises a holder for the subject (59) and four mounts (60), each designed to mount MRI-compatible camera (44).

Figure 8:
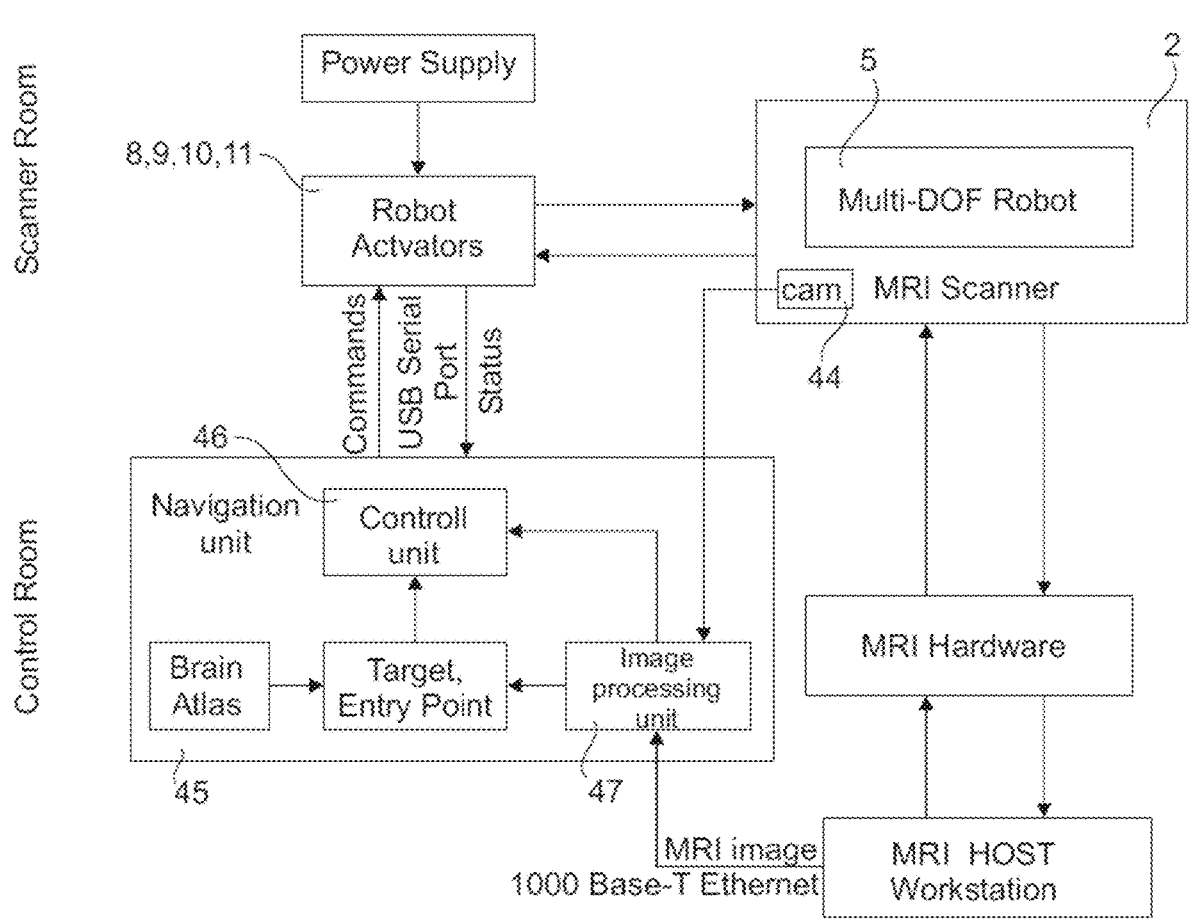
FIG. 8 shows the principle function of the positioning system according to one embodiment and an MRI-system.

The positioning system further comprises a navigation unit (45), comprising a control unit (46), which controls the motion of the first (8), second (9), third (10) and fourth (11) actuator, an image processing unit (47), which processes real time images of the imaging device (2) and/or the at least one camera (44) in the bore (4). FIG. 8 shows the principle function of the positioning system and an MRI-system.

The MRI-system comprises a Host Workstation and MRI-Hardware which communicate with the MRI-scanner. In which the multi DOF (degrees of freedom) robot of the positioning system (1) is arranged. The Host Workstation communicates via a 1000 Base-T Ethernet with the image processing unit (47) of the navigation unit (45). In particular the MRI-images are sent in real time to the image processing unit (47). Further, the at least one camera (44) sends images to the image processing unit (47). The navigation unit (45) further comprises a brain atlas and a control unit (46). The control unit (46) communicates with the actuators (8, 9, 10, 11) via USB Serial bus. This communication comprises control commands from the control unit (46) to the actuators (8, 9, 10, 11) and a position feedback from the actuators (8, 9, 10, 11) to the control unit (46). Eventually a power supply is provided for the power supply of the actuators (8, 9, 10, 11). The power supply, the actuators (8, 9, 10, 11) and the MRI-scanner are placed in the scanner room. The Host Workstation, MRI-Hardware and the navigation unit (45) are placed in a control room.

These components may be applied for a method to position an insertion element (3) using a positioning system (1) according to any one of the preceding embodiments in a MR imaging device (2):

a. Lowering the insertion element (3) by the robot (5) to a first position on the subject or close to the subject;

b. Acquiring a 3D-MRI image and process the image via the image processing unit (47) to identify the location of subject, as well as the position of insertion element;

c. Calculation of the coordinates of the target point and the insertion element (3) and calculation of an optimized movement trajectory for the insertion element (3) by the control unit (46);

d. Monitoring movement trajectory by real-time MRI image via the image processing unit (47).

In the following, working results are presented on tests of said positioning system and method.

Figure 9:
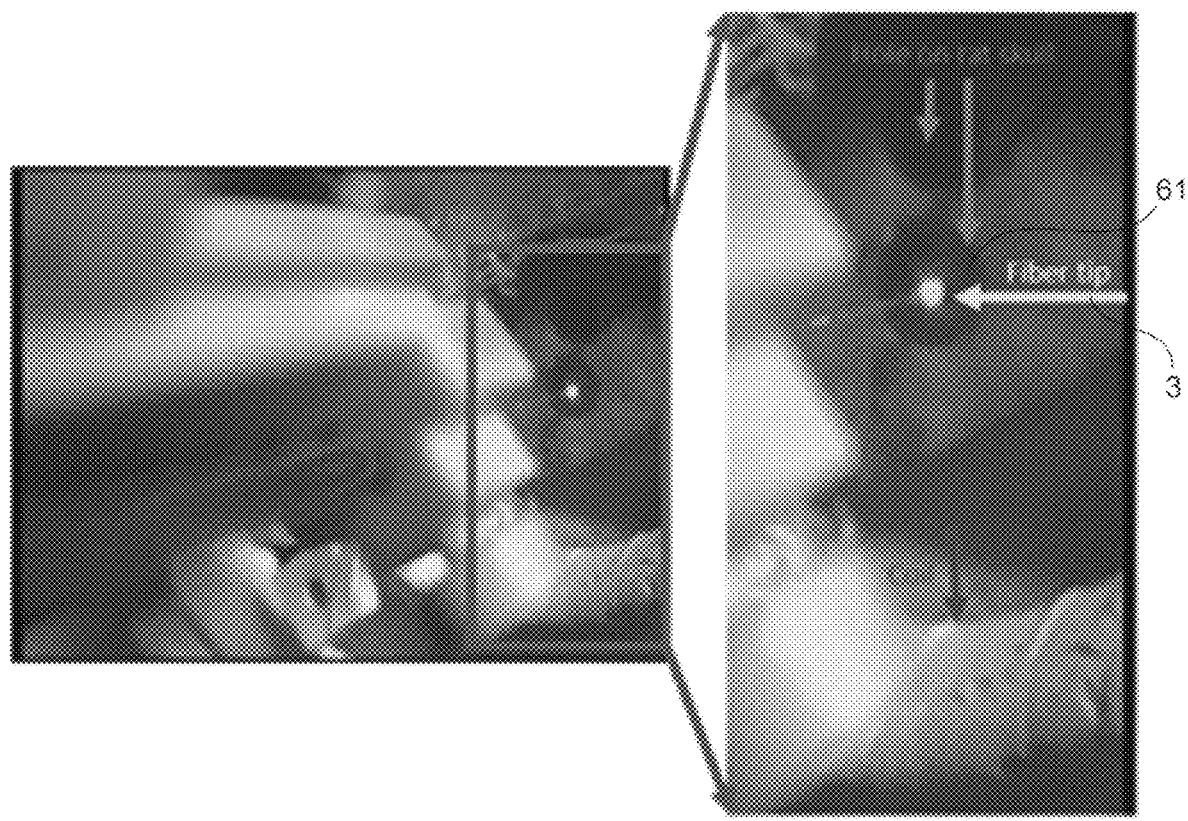
FIG. 9 shows an image of a fiber position above a hole in a rat skull.

FIG. 9 shows an image by MRI-compatible cameras (44) of a fiber position above a hole in a rat skull. Two cameras (44) are positioned to obtain visual guidance of the brain intervention. Camera-based visual signals are presented in the navigation unit (45). Thus, an operator can monitor the real time situation inside the MRI-scanner (2). After the operator can clearly see the fiber (3) above the rat brain, and the hole in the skull (61), a laser is switched on. The light from the tip (3a) can be used as a marker of fiber tip (3a) for further 3D registration with MRI images (visual cue-based 3D registration will be solved by script with self-design algorithm). The operator could also manually adjust the probe position to target the craniotomy window above the animal skull.

Firstly, the fiber (3) will be moved to be above the hole (61) on the rat skull using the third (10) and fourth actuators (11). Secondly, the operator sets the steps and distance for the final movement, down to the brain using the first actuator (8) and the second actuator for holding the angle position (9). In parallel, the real time camera signals are displayed.

Figure 10A:
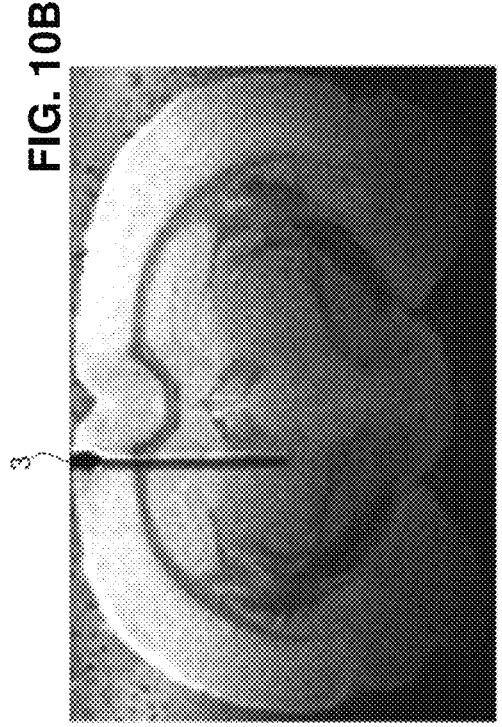
FIGS. 10A-10D show a fiber placement of perfused rat brain in vitro.
Figure 10B:
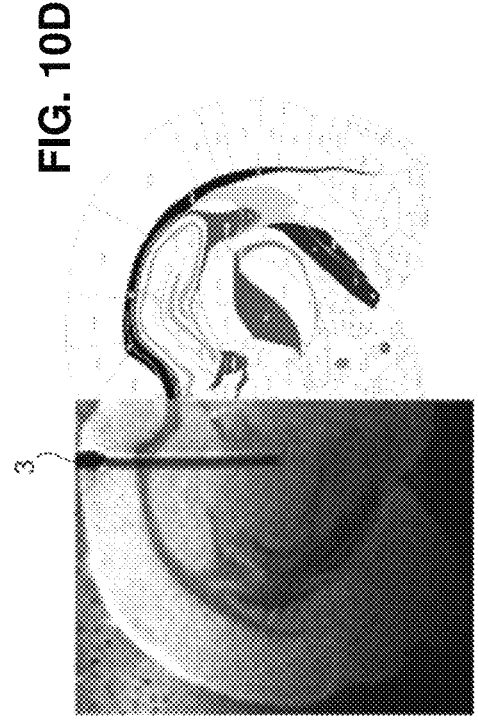
Figure 10C:
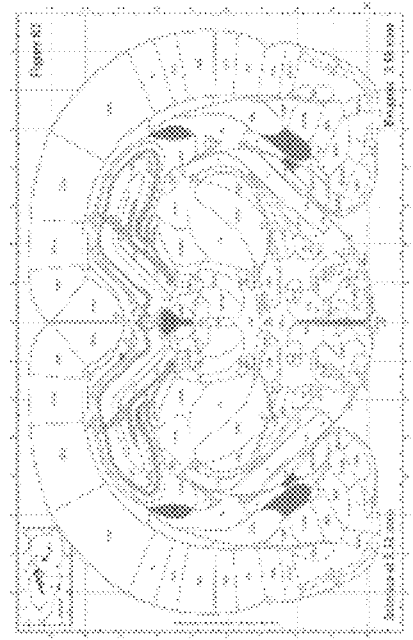
Figure 10D:
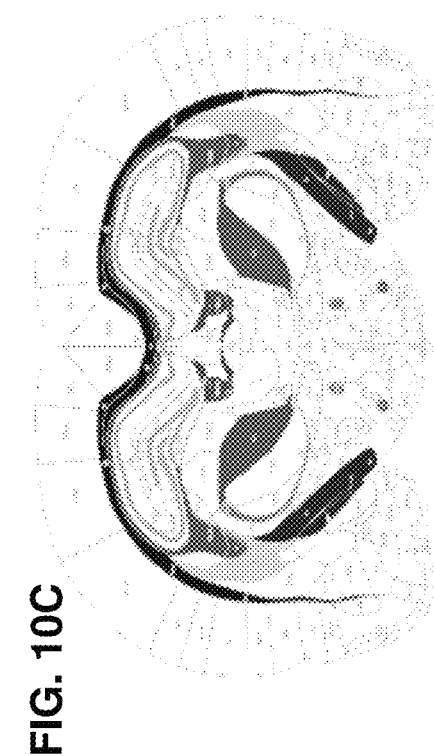

FIGS. 10A-10D present a fiber (3) placement of perfused rat brain in vitro. The capability to place the fiber (3) with different depth is particularly useful to target multiple sites along the insertion path. FIG. 10A shows the targeting position in the rat brain atlas with the bregma and Interaural position: −3.48 mm and 5.52 mm, respectively. FIG. 10B shows the fiber location in the targeted brain region, centrolateral thalamic nucleus (CL), which is illustrated in FIG. 10D.

Figure 11:
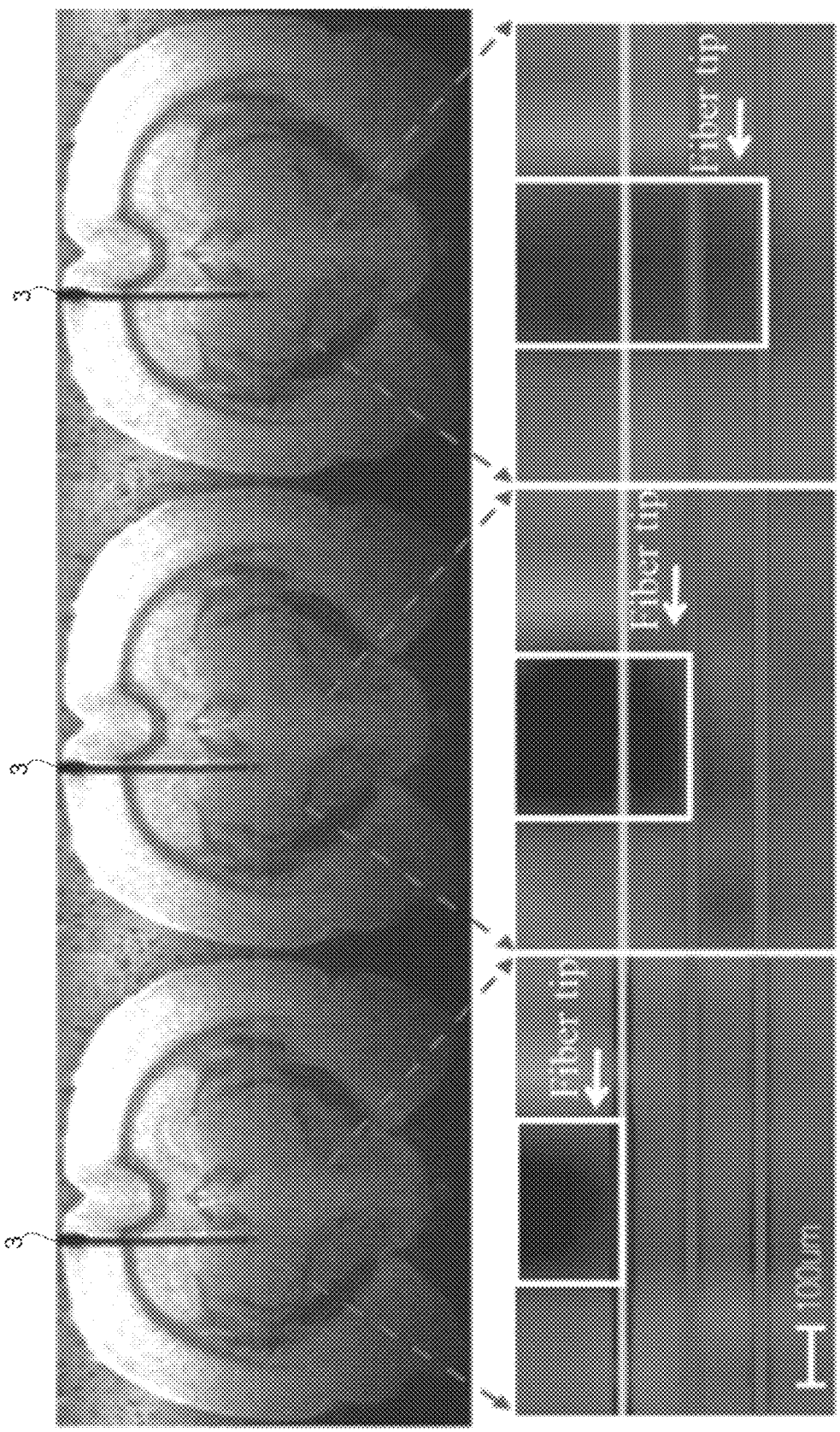
FIG. 11 shows a fiber placement of perfused rat brain in vitro with different moving distances.

FIG. 11 shows three images with two actuator (8) steps (with a step distance of 100 μm) to clarify the precision of the robot (5). Three continuous MRI images with step distance 100 μm. Because the MRI resolution is 100 μm, it can be seen that every step of the fiber (3) moving distance is approximately 100 μm. At each step, the fiber (3) was one line of voxel deeper. Meanwhile, this distance difference was maintained through the whole fiber insertion procedure.

Figure 12:
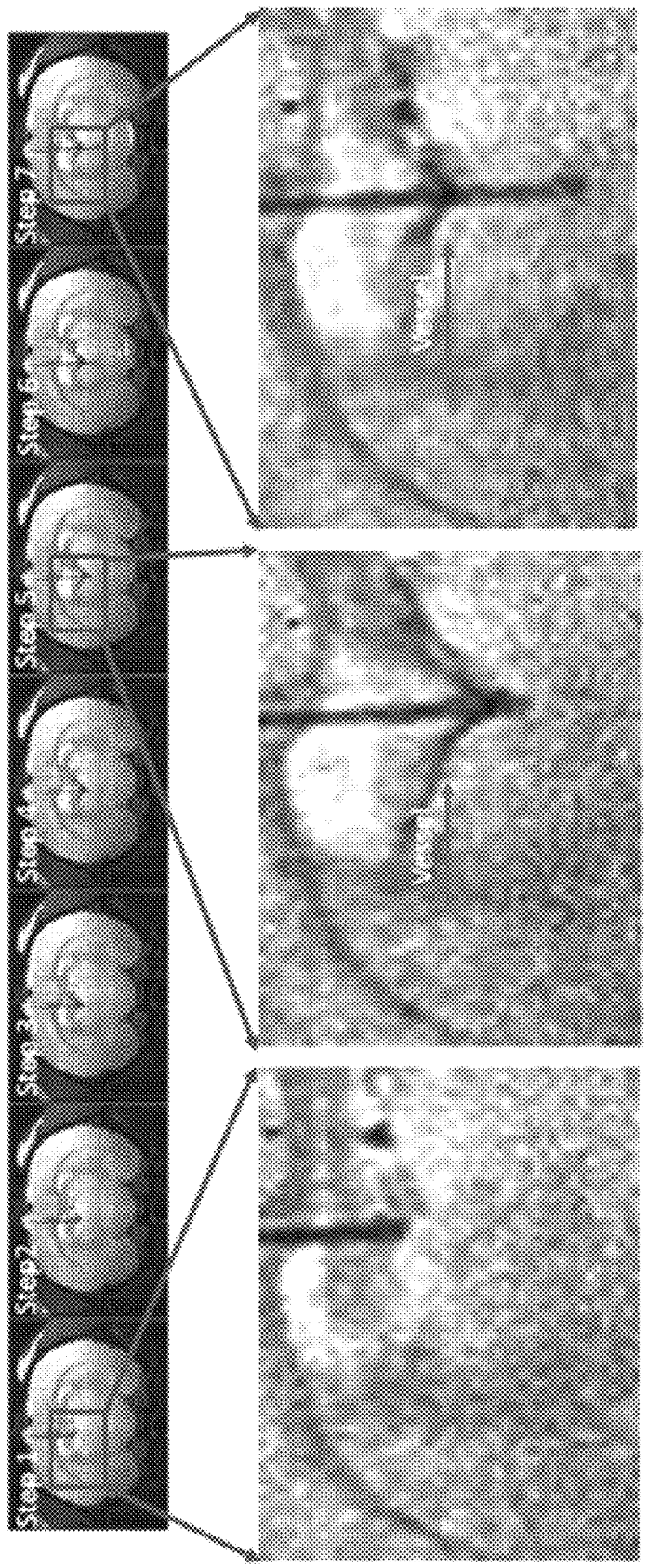
FIG. 12 shows time-lapsed images of fiber optic targeting in the rat brain in vivo.

FIG. 12 shows time-lapsed images of fiber optic targeting in the rat brain in vivo. In this application, the damage of the brain is visible during the insertion, as illustrated in FIG. 12. When the fiber tip (3a) touched the ventricle, the pushing force caused deformation of the parenchyma tissue of the ventricle border, but lead tissue bleeding. After penetrating the ventricle, the fiber (3) was further deepened to target the subcortical regions in the rat brain.

All the features disclosed in the application documents are claimed as being essential to the invention if, individually or in combination, they are novel over the prior art.

LIST OF REFERENCE NUMERALS 1 positioning system
2 imaging device
3 insertion element
3a end portion of the insertion element
4 bore of the imaging device
5 robot
6 head part of the robot
7 holding element
7a body of the holding element
7b gripping portion holding element
8 first actuator
9 second actuator
10 third actuator
11 fourth actuator
12 first drive mechanism
13 second drive mechanism
14 first pulley
14a teeth of first pulley
15 first belt
15a teeth of first belt
16 shaft
17 central hub portion of the first pulley
18 converting element
19 rotational motion of the first pulley
20 linear motion of the holding element along the A-axis
21 disc-like element
21a center of the disc-like element
21b edge of the disc-like element
22 first surface of disc-like element
23 first guiding element
24 second guiding element
24a second guiding element one
24b second guiding element two
24c second guiding element three
25 spiral
25a space between two opposing points of the spiral
26 second pulley
26a teeth of second pulley
27 second belt
27a teeth of second belt
28 cup-like element
28a inner space of the cup-like element
28b frontal part of the cup-like element
29 third guiding element
30 rotational motion of the cup-like element 31 pivoting-motion of the holding element
32 holding rod
32a tube-like end portion of the holding rod
33 connection element
33a loop portion of the connection element
33b insertion portion of the connection element
34 third drive mechanism
35 fourth drive mechanism
36 third pulley
36a teeth of third pulley
37 third belt
37a teeth of third belt
38 threaded spindle
39 nut
40 platform
41 head part of the platform
42 foot part of the platform
43 holder
44 camera
45 navigation unit
46 control unit
47 image processing unit
48 support device
49 fixing element
50 pulley connected to the first actuator
51 second surface of disc-like element
52a, 52b guiding projections
53 direction
54a, 54b grooves
55 pulley connected to the second actuator
56 first translation stage
57 mounting element
58 bearings
59 holder for subject
60 mount MRI-compatible camera
61 hole in the skull
62 second translation stage
X-axis
Y-axis
Z-axis
A-axis
B-axis
α angle

We claim:

1. A positioning system for positioning an insertion element on or in the body of a subject, the positioning system comprising an imaging device, wherein the imaging device comprises a bore, in which the subject is received, wherein the positioning system further comprising a robot, which is at least partially arranged in the bore of the imaging device and comprises a holding element to hold the insertion element; wherein
the robot further comprises at least one actuator, wherein said at least one actuator is arranged with a distance D from the bore to minimize magnetic and/or electromagnetic interferences between the imaging device and a first actuator of the at least one actuator, wherein said distance D is between 1.5 and 4.7 meters, and said first actuator is coupled to the holding element in a form-fit- and/or a force-fit-manner;
wherein the coupling of the first actuator to the holding element in the form-fit and/or the force-fit-manner is achieved by a belt drive, wherein a first belt is looped over a first pulley and a pulley connected to the first actuator, and wherein the connection between the first belt and the first pulley is in a form-fit manner and said first actuator acts on the holding element via the first belt and first pulley such that the end portion of the insertion element is linearly movable;
wherein the bore has a longitudinal expansion along an X-axis and further expands along a Z-axis and a Y-axis, wherein said X-axis, Y-axis and Z-axis are orthogonal to each other, wherein at least the end portion of the insertion element has a longitudinal extension along an A-axis, wherein the A-axis and the Z-axis form an angle α, which is in the range between −90° and +90°;
wherein the robot comprises a head part, a first and a second drive mechanism, wherein the first actuator acts on the holding element via the first drive mechanism such that the end portion of the insertion element is linearly movable along the A-axis, wherein a second actuator of the at least one actuator acts on the holding element via the second drive mechanism such that the end portion of the insertion element can be pivoted about a pivot axis B, wherein by said pivoting-motion the angle α is adjusted; and
wherein the second drive mechanism comprises a second pulley, which is connected to the second actuator by a second belt, and a cup element, which is rigidly connected to the second pulley, wherein the cup element comprises a receiving element, which extends along an A-axis and receives the holding element, wherein the cup element engages the holding element such that a rotational motion of the cup element causes a pivoting-motion of the holding element around a B-axis.

2. The positioning system according to claim 1, wherein the imaging device is a functional magnetic resonance imaging (fMRI)-device comprising a magnetic resonance imaging (MRI) scanner, using a magnetic field in the range of ca. 3 T to ca. 21 T, and a bore diameter in the range of 12 cm to 6 cm, wherein the insertion element is selected from the group consisting of: a fiber-optic for optogenetic stimulation and fluorescent recording from endogenous biosensors of metabolites of the subject brain or exogenous biosensors of metabolites of the subject brain, an electrode for recording electrophysiological or electrochemical signal, and an implantable pump or needle for direct drug delivery to treat tumor or other diseases.

3. The positioning system according to claim 1, wherein the first drive mechanism comprises the first pulley, which is connected to the first actuator by the first belt, a shaft, which is received in a central hub portion of the first pulley and connects the first pulley and a converting element, on which the holding element is mounted, wherein the converting element converts a rotational motion of the first pulley into a linear motion of the holding element along the A-axis.

4. The positioning system according to claim 3, wherein the converting element comprises a disc element with a first surface on which a first guiding element is arranged, wherein the holding element comprises at least one second guiding element, which engages the first guiding element.

5. The positioning system according to claim 4, wherein the first guiding element has a continuous course, which originates in or in the proximity of a center of the disc element, wherein the continuous course evolves in form of a spiral to an edge of the disc element, wherein the spiral is described by a polar equation of $r = a*\theta$, wherein r is the radial distance, θ is the polar angle and a is a constant >0.

6. The positioning system according to claim 1, wherein the head part of the robot is connected to a holding rod via a connection element, wherein the robot further comprises a third actuator of the at least one actuator which acts on the holding rod via a third drive mechanism, such that the head part of the robot can be moved along the Y-axis, wherein the robot further comprises a fourth actuator of the at least one actuator which acts on the holding rod via a fourth drive mechanism, such that the head part of the robot can be moved along the X-axis.

7. The positioning system according to claim 6, wherein the third drive mechanism comprises a third pulley, which is connected to the third actuator by a third belt, wherein the third pulley is rigidly connected to a threaded spindle on which a nut is arranged, wherein the nut is connected to the holding rod of the robot, wherein the threaded spindle is arranged perpendicularly to the holding rod, wherein a rotation of the third pulley causes a rotation of the threaded spindle and a movement of the nut and the holding rod along the Y-axis.

8. The positioning system according to claim 7, wherein the positioning system comprises a platform, on which the robot is arranged, wherein the subject is suspended and/or held at a head part of the platform, which can be arranged in the bore of the imaging device, wherein the first, second, third and fourth actuators are arranged at a foot part of the platform, wherein the threaded spindle is arranged on a holder connected to the platform.

9. The positioning system according to claim 8, wherein the robot and the platform mainly consist of MRI-compatible materials, such as nonmagnetic, dielectric materials, plastics, rubbers, ceramics.

10. The positioning system according to claim 8, wherein the positioning system comprises at least one MRI-compatible camera, which is mounted on the head part of the platform.

11. The positioning system according to claim 8, wherein the positioning system further comprises a navigation unit comprising a control unit, which controls the motion of the first, second, third and fourth actuator, an image processing unit, which processes real time images of the imaging device and/or an at least one camera in the bore.

12. A method to position an insertion element using a positioning system according to claim 1 in a magnetic resonance (MR) imaging device, the method comprising the steps of:
  a. lowering the insertion element by the robot to a first position on the subject or close to the subject;
  b. acquiring a three-dimensional-magnetic resonance imaging (3D-MRI) image and processing the image via an image processing unit to identify the location of the subject, as well as the position of the insertion element;
  c. calculating the coordinates of a target point and the insertion element and calculating an optimized movement trajectory for the insertion element by a control unit;
  d. monitoring the movement trajectory by the real-time MRI image via the image processing unit.

13. A positioning system for positioning an insertion element on or in the body of a subject, the positioning system comprising an imaging device, wherein the imaging device comprises a bore, in which the subject is received, wherein the positioning system further comprising a robot, which is at least partially arranged in the bore of the imaging device and comprises a holding element to hold the insertion element; wherein
  the robot further comprises at least one actuator, wherein said at least one actuator is arranged with a distance D from the bore to minimize magnetic and/or electromagnetic interferences between the imaging device and a first actuator of the at least one actuator, wherein said distance D is between 1.5 and 4.7 meters, and said first actuator is coupled to the holding element in a form-fit-and/or a force-fit-manner;
  wherein the coupling of the first actuator to the holding element in the form-fit and/or the force-fit-manner is achieved by a belt drive, wherein a first belt is looped over a first pulley and a pulley connected to the first actuator, and wherein the connection between the first belt and the first pulley is in a form-fit manner and said first actuator acts on the holding element via the first belt and first pulley such that the end portion of the insertion element is linearly movable;
  wherein the bore has a longitudinal expansion along an X-axis and further expands along a Z-axis and a Y-axis, wherein said X-axis, Y-axis and Z-axis are orthogonal to each other, wherein at least the end portion of the insertion element has a longitudinal extension along an A-axis, wherein the A-axis and the Z-axis form an angle $\alpha$, which is in the range between 0° and ±90°;
  wherein the robot comprises a head part, a first and a second drive mechanism, wherein the first actuator acts on the holding element via the first drive mechanism such that the end portion of the insertion element is linearly movable along the A-axis, wherein a second actuator of the at least one actuator acts on the holding element via the second drive mechanism such that the end portion of the insertion element can be pivoted about a pivot axis B, wherein by said pivoting-motion the angle $\alpha$ is adjusted;
  the head part of the robot is connected to a holding rod via a connection element, wherein the robot further comprises a third actuator of the at least one actuator which acts on the holding rod via a third drive mechanism, such that the head part of the robot can be moved along the Y-axis, wherein the robot further comprises a fourth actuator of the at least one actuator which acts on the holding rod via a fourth drive mechanism, such that the head part of the robot can be moved along the X-axis;
  the third drive mechanism comprises a third pulley, which is connected to the third actuator by a third belt, wherein the third pulley is rigidly connected to a threaded spindle on which a nut is arranged, wherein the nut is connected to the holding rod of the robot, wherein the threaded spindle is arranged perpendicularly to the holding rod, wherein a rotation of the third pulley causes a rotation of the threaded spindle and a movement of the nut and the holding rod along the Y-axis.

14. The positioning system according to claim 13, wherein
  the imaging device is a functional magnetic resonance imaging (fMRI)-device comprising a magnetic resonance imaging (MRI) scanner, using a magnetic field in the range of ca. 3 T to ca. 21 T, and a bore diameter in the range of 12 cm to 6 cm, wherein the insertion element is selected from the group consisting of: a fiber-optic for optogenetic stimulation and fluorescent recording from endogenous biosensors of metabolites of the subject brain or exogenous biosensors of metabolites of the subject brain, an electrode for recording electrophysiological or electrochemical signal, and an implantable pump or needle for direct drug delivery to treat tumor or other diseases.

15. The positioning system according to claim 13, wherein
the first drive mechanism comprises the first pulley, which is connected to the first actuator by the first belt, a shaft, which is received in a central hub portion of the first pulley and connects the first pulley and a converting element, on which the holding element is mounted, wherein the converting element converts a rotational motion of the first pulley into a linear motion of the holding element along the A-axis.

16. The positioning system according to claim 13; wherein
the first guiding element has a continuous course, which originates in or in the proximity of a center of the disc element, wherein the continuous course evolves in form of a spiral to an edge of the disc element, wherein the spiral is described by a polar equation of $r=a*\theta$, wherein r is the radial distance, $\theta$ is the polar angle and a is a constant >0.

17. The positioning system according to claim 13, wherein
the positioning system comprises a platform, on which the robot is arranged, wherein the subject is suspended and/or held at a head part of the platform, which can be arranged in the bore of the imaging device, wherein the first, second, third and fourth actuators are arranged at a foot part of the platform, wherein the threaded spindle is arranged on a holder connected to the platform.

18. The positioning system according to claim 17, wherein
the robot and the platform mainly consist of MRI-compatible materials, such as nonmagnetic, dielectric materials, plastics, rubbers, ceramics.

19. The positioning system according to claim 17, wherein
the positioning system comprises at least one MRI-compatible camera, which is mounted on the head part of the platform, wherein the positioning system further comprises a navigation unit comprising a control unit, which controls the motion of the first, second, third and fourth actuator, an image processing unit, which processes real time images of the imaging device and/or an at least one camera in the bore.

20. A method to position an insertion element using a positioning system according to claim 13 in a magnetic resonance (MR) imaging device, the method comprising the steps of:
a. lowering the insertion element by the robot to a first position on the subject or close to the subject;
b. acquiring a three-dimensional-magnetic resonance imaging (3D-MRI) image and processing the image via an image processing unit to identify the location of the subject, as well as the position of the insertion element;
c. calculating the coordinates of a target point and the insertion element and calculating an optimized movement trajectory for the insertion element by a control unit;
d. monitoring the movement trajectory by the real-time MRI image via the image processing unit.

* * * * *